(12) United States Patent
Merenov et al.

(10) Patent No.: US 9,481,629 B2
(45) Date of Patent: Nov. 1, 2016

(54) PROCESS FOR THE PRODUCTION OF HIGH PURITY GLYCOL ESTERS

(71) Applicant: Dow Global Technologies LLC, Midland, MI (US)

(72) Inventors: Andrei S. Merenov, Lake Jackson, TX (US); Edward D. Daugs, Midland, MI (US); Patrick Ho Sing Au-Yeung, Midland, MI (US); Jason L. Trumble, Bay City, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/430,719

(22) PCT Filed: Sep. 24, 2013

(86) PCT No.: PCT/US2013/061368
§ 371 (c)(1),
(2) Date: Mar. 24, 2015

(87) PCT Pub. No.: WO2014/052298
PCT Pub. Date: Apr. 3, 2014

(65) Prior Publication Data
US 2015/0274635 A1 Oct. 1, 2015

Related U.S. Application Data

(60) Provisional application No. 61/706,835, filed on Sep. 28, 2012.

(51) Int. Cl.
*C07C 69/76* (2006.01)
*C07C 67/54* (2006.01)
*C07C 67/08* (2006.01)

(52) U.S. Cl.
CPC ............... *C07C 67/54* (2013.01); *C07C 67/08* (2013.01)

(58) Field of Classification Search
CPC ........ C07C 67/08; C07C 67/54; C07C 69/78
See application file for complete search history.

(56) References Cited

U.S. PATENT DOCUMENTS

| | | | |
|---|---|---|---|
| 4,658,003 A | 4/1987 | Schmidt et al. | |
| 4,733,005 A | 3/1988 | Schmidt et al. | |
| 7,118,653 B2 | 10/2006 | Brady et al. | |
| 7,956,157 B2 | 6/2011 | Butler | |
| 8,932,434 B2 | 1/2015 | Lee et al. | |
| 2009/0288939 A1* | 11/2009 | Smith | B01D 3/14 202/158 |
| 2010/0112362 A1 | 5/2010 | Craciun et al. | |

FOREIGN PATENT DOCUMENTS

| | | | |
|---|---|---|---|
| CN | 1169421 A | | 1/1998 |
| DE | 19618152 | * | 8/1997 |
| JP | 199103050246 | * | 3/1991 |

OTHER PUBLICATIONS 152 translated 1997.*
246 translated 1991.*
Bassam, Journal of Molecular Catalysis A: Chemical, 2001; vol. 165, No. 1-2, p. 283-290.
Conn, Journal of the American Chemical Society, 1932, vol. 54, No. 11, p. 4370-4372.
Kuhn, Journal of the American Chemical Society, 1948, vol. 70, No. 10, p. 3370-3375.
Mamedov, Sbornik Trudov—Akademiya Nauk Azerbaidzhanskoi SSR, Institut Neftekhimicheskish Protsessov, Database CASREACT, 1975, 6, 51-8 Abstract.
Marchal, Journal of Organic Chemistry, 1995, vol. 60, No. 26, p. 8336-8340.
PCT/US2013/061368, 20140704, International Search Report and Written Opinion.
PCT/US2013/061368, 20150409, International Preliminary Report on Patentability.
Hernandez, et al., "Implementation and Operation of a Dividing-Wall Distillation Column", Chemical Engineering & Technology, 2011, 34, No. 5, p. 746-750.
Sandoval-Vergara, et al., "Implementation of a Reactive Dividing Wall Distillation Column in a Pilot Plant", Computer-Aided Chemical Engineering, 25 (18th European Symposium on Computer Aided Process Engineering, 2008) ESCAPE 18, p. 229-234.
Smith, "Review of Glycol Ether and Glycol Ether Ester Solvents Used in the Coating Industry", Environmental health perspectives (1984), 57, p. 1-4.

* cited by examiner

*Primary Examiner* — Yevegeny Valenrod
*Assistant Examiner* — Blaine G Doletski

(57) ABSTRACT

A process for the production of 2-butoxyethyl benzoate from benzoic acid and 2-butoxy ethanol wherein at least a portion of the crude reaction product is fed to a distillation column comprising a dividing wall or a pasteurizing section.

10 Claims, 3 Drawing Sheets

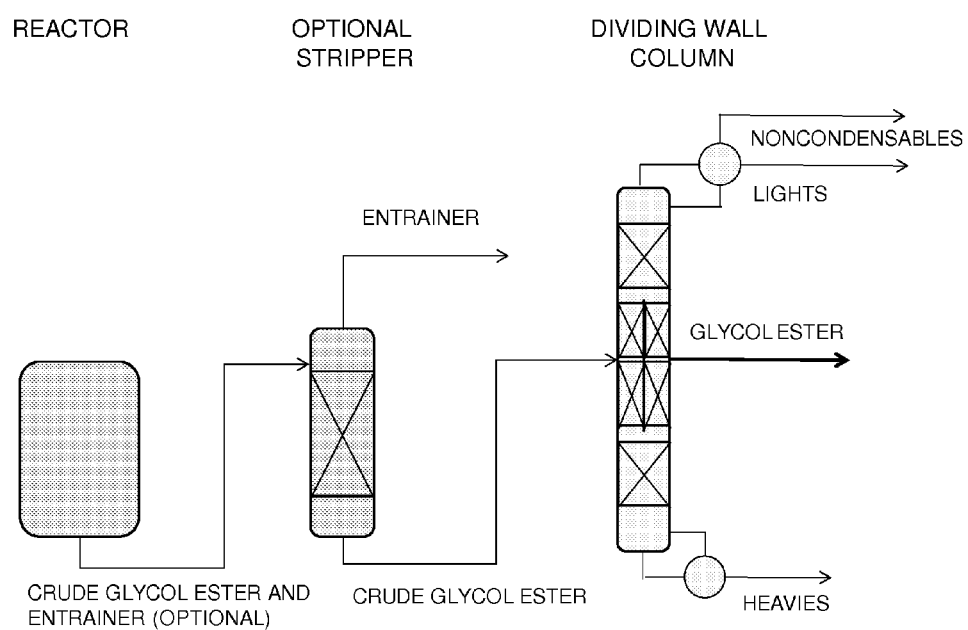
Figure 1. Schematic of Distillation Process Using Dividing Wall Column.

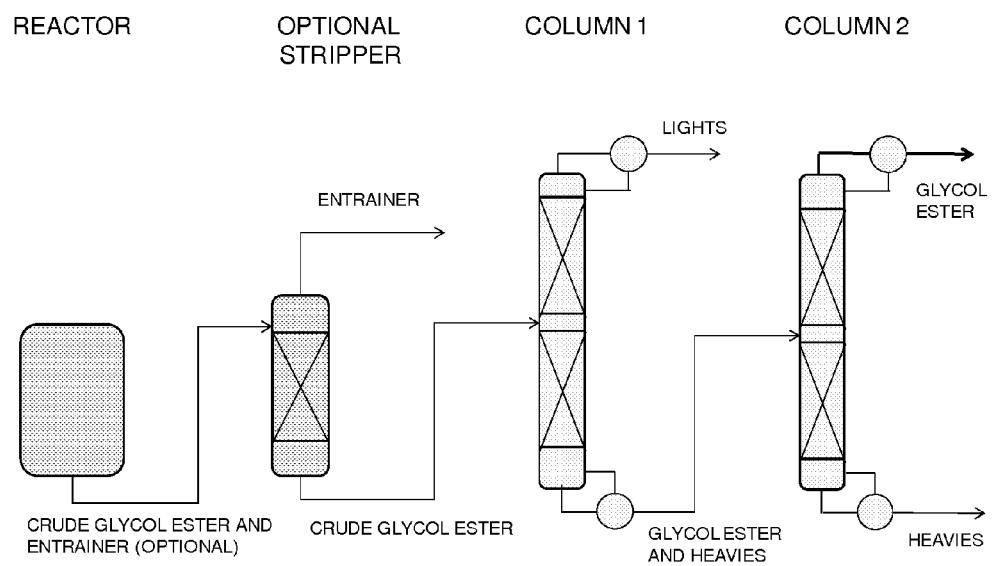
Figure 2. Schematic of Conventional Distillation Process.

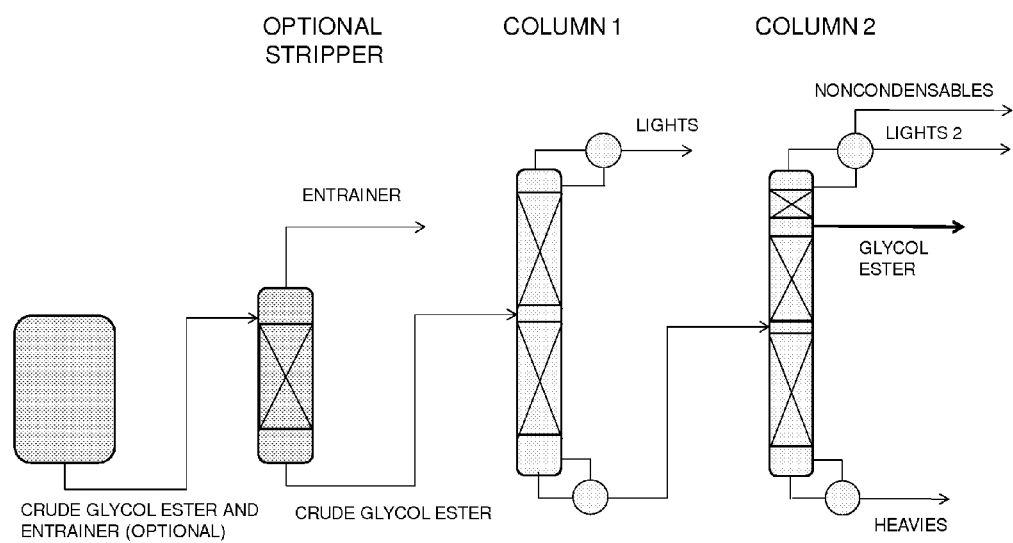
Figure 3. Schematic of Distillation Process with a Pasteurizing Section.

PROCESS FOR THE PRODUCTION OF HIGH PURITY GLYCOL ESTERS

CROSS-REFERENCE TO RELATED APPLICATIONS

This application claims priority from provisional application Ser. No. 61/706,835, filed Sep. 28, 2012, which is incorporated herein by reference in its entirety.

BACKGROUND OF THE INVENTION

The invention relates to a process for producing heavy glycol esters in high purity.

Glycol esters with low VOC, and therefore high boiling points, are used as solvents in coating applications. It is important that these esters have low color and low odor. Therefore, it is important that the glycol esters have a low content of heavy impurities, which are commonly associated with undesired color, and light impurities, which are commonly associated with odor. Another aspect of the usage of glycol esters in coating applications is the cost of the material; due to the nature of the applications, the cost of glycol esters should not exceed the cost of similar materials commonly used in coating formulations. Therefore it would be desirable to have a process for the manufacture of high purity esters, which process would require reduced capital and have reduced energy consumption.

SUMMARY OF THE INVENTION

The invention is such process comprising: (a) contacting benzoic acid and 2-butoxy ethanol under reaction conditions to produce a crude product comprising 2-butoxyethyl benzoate and impurities; (b) feeding at least a portion of the crude product to a distillation column comprising a dividing wall or a pasteurizing section; removing an overhead stream and a bottoms stream from the distillation column, and removing a side draw stream from the distillation column; wherein, in the case where a dividing wall is present, the crude product enters the dividing wall distillation column on an opposing side of the dividing wall from the side draw stream.

Surprisingly, the use of a distillation column comprising a dividing wall or pasteurizing section allows the production of ultra pure 2-butoxyethyl benzoate with controlled amounts of impurities, specifically butanal.

BRIEF DESCRIPTION OF THE DRAWINGS

FIG. 1 is a schematic of a process of the invention using a dividing wall column.

FIG. 2 is a schematic of a conventional distillation process.

FIG. 3 is a schematic of a process of the invention using a pasteurizing section.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

As used herein, the term "heptane" includes isomeric mixtures of heptane.

As used herein, the term "feeding at least a portion of the crude product to a distillation column comprising a dividing wall or a pasteurizing section" is intended to cover the situation in which at least part of the crude product passes through other process equipment, including equipment that may separate various components therefrom, before entering the distillation column comprising a dividing wall or a pasteurizing section.

Disclosed herein is a process for the production of 2-butoxyethyl benzoate wherein a reactor produces a reactor effluent stream, wherein at least a portion of the reactor effluent stream is sent, directly or indirectly, to a distillation column, and wherein the column comprises a dividing wall or a pasteurization section. In the case of a dividing wall distillation column, the dividing wall distillation column can produce a light cut, a heavy cut, and a 2-butoxyethyl benzoate stream.

The process of the invention employs benzoic acid and 2-butoxy ethanol, and optionally an acid catalyst, to produce 2-butoxyethyl benzoate.

The starting materials employed are well known materials and are widely commercially available. For example, 2-butoxy ethanol is available from The Dow Chemical Company under the tradename Butyl CELLOSOLVE. Commercial grade benzoic acid and 2-butoxy ethanol can be employed.

The reactants are employed in amounts sufficient to produce the desired product 2-butoxyethyl benzoate. The molar ratio of 2-butoxy ethanol to benzoic acid advantageously is from less than 0.1 to 10, preferably is from 0.8 to 1.2, and more preferably is approximately 1.

A catalytic amount of the optional acid catalyst may be employed as desired. The catalyst is an acid catalyst for the underlying reaction. A wide variety of acids are suitable. Examples of the catalyst include, sulfuric acid, sulfonic acids, phosphoric acid, and acidic ion exchange resins. Mixtures of acids can be employed. Advantageously, from about 100 ppm to 5% of catalyst is employed based on the weight of the reactive mixture. Preferably, the amount of catalyst is from 0.3 to 0.5% by weight.

The reaction can be conducted at from 70° C. to 190° C. at a pressure of from 2000 mmHg to 1 mmHg. The pressure and temperature may change as the reaction progresses.

The reaction is reversible and produces the glycol ester, with water as a by-product. In order to increase the reaction rate and conversion, water advantageously is removed from the reaction zone, either constantly or intermittently. A suitable entraining agent, for example heptane, optionally can be used to enhance the water removal from the reaction zone. In general, an entrainer can be selected from wide class of chemicals including but not limited to straight paraffins, glycol ethers or other chemicals producing heterogeneous azeotropes with water and having lower boiling point than 2-butoxyethanol. It is important to note that an excess of 2-butoxyethanol can be also used as the entrainer to remove water from the reactive system. The latter is especially advantageous because no additional chemicals are introducing in the process. Mixtures of entraining agents can be employed.

The reaction of 2-butoxyethanol with benzoic acid in the presence of sulfuric acid to produce 2-butoxyethyl benzoate is an esterification reaction. The reactor effluent contains low boiling impurities, higher boiling impurities, water and, if employed, the catalyst. The glycol ester should be separated from the reactor effluent in order to be used in coating applications. In one embodiment of the invention, the catalyst is neutralized prior to distillation.

Advantageously, when an entrainer is used to enhance water removal from the reactor effluent, the effluent can be sent to an optional stripper to reduce the amount of entrainer that enters the dividing wall column. A wide variety of devices can be employed as the stripper, and can be chosen and operated according to criteria well known to those skilled in the art. For example, a packed column, a trayed column, a rolled film evaporator and a thin film evaporator are examples of devices that can be used as the optional stripper.

In one embodiment of the invention, the stripper effluent, i.e. a material with a reduced amount of the entrainer, or the reactor effluent is sent to a dividing wall column, where the lighter, low boiling impurities are removed from the material as the top product, and heavier, higher boiling impurities are removed from the material as the bottom product, and the high purity glycol ester is produced as the middle product. The use of a dividing wall column allows substantial energy and capital saving in the separation step of the process. A schematic of this embodiment is shown in FIG. 1.

Of particular importance to the preparation of high purity glycol esters is the formation of lighter, low boiling impurities, and in particular the odor-causing component butyraldehyde (butanal), during the distillation process by the thermal or oxidative decomposition of heavier components. The continuous formation of lighter boiling components during the distillation process compromises the ability of a conventional batch or continuous distillation, wherein the lighter components are removed overhead as a first distillation cut before the glycol ester is removed overhead as a product cut, to produce high purity glycol ester free of lower boiling, odor causing, components.

The dividing wall distillation column comprises a dividing wall. The dividing wall vertically bisects a portion of the interior of the distillation column but does not extend to the top or bottom sections of the column, thus enabling the column to be refluxed and reboiled similar to a conventional column. The dividing wall provides a fluid impermeable baffle separating the interior of the column. The feed inlet to the column is located on one side of the dividing wall while one or more side draws are located on the opposing side. The dividing wall enables the side of the column that does not have the inlet to function in a more stable manner with minimal effect from fluctuations in inlet flow rates, conditions or composition. This increased stability enables the column to be designed and operated in a manner that allows one or more side draw streams having different compositions from either the overhead stream or the bottoms stream to be removed from the column.

The temperature and pressure in the distillation column is dependent on the composition of the material being distilled. In one embodiment of the invention, the column is operated at reduced pressure, such as from about 1 to about 50 mmHg, or from 5 to 10 mmHg. The reboiler temperature advantageously is from 120 to 195° C.

The ability to make three or more product streams from a single column can enable component separation with fewer distillation columns and possibly reduced capital costs. The dividing wall distillation column can be used as a sole distillation column or multiple dividing wall distillation columns can be employed, either in series or parallel arrangements. The dividing wall distillation column can also be used in conjunction with one or more conventional distillation columns or separation devices. Embodiments of the invention can be particularly applicable when the optimum feed location to the column is above the optimum side draw location. If the feed location is above the side draw location in a conventional distillation column, the downward flow of the liquid feed within the column will have a significant effect on the side draw composition. Variations in the feed flow rate, conditions or composition of the feed stream will alter the side draw composition and make the production of a stable side draw stream very difficult to achieve in this configuration of a conventional distillation column.

In one embodiment of the invention, the column where the final product is made comprises a pasteurizing section at the top of the column. The purpose of the pasteurizing section is: (1) to concentrate light impurities such as, for example butanal, in the overhead stream, and (2) to remove the impurities from the final product that is withdrawn as a side stream below the pasteurizing section. The pasteurizing section advantageously includes several separation stages, or theoretical trays.

The type of distillation apparatus can be selected according to criteria well known to those skilled in the art. For example, a distillation column can include trays or packing, such as low pressure drop wire gauze structured packing, e.g., in the pasteurizing section and/or throughout the distillation apparatus.

Advantageously, the process of the invention provides a product that is low in butanal content. For example, the butanal content of the 2-butoxyethyl benzoate can be less than 200 ppm, less than 50 ppm, less than 10 ppm, less than 5 ppm, or less than 1 ppm by weight.

Specific Embodiments of the Invention

The following examples are given to illustrate the invention and should not be construed as limiting its scope.

PREPARATION 1

Crude 2-Butoxyethyl Benzoate

A batch of crude 2-butoxyethyl benzoate is prepared by reacting 8.2 kg (67 mol) of benzoic acid and 8.5 kg (72 mol) of Butyl CELLOSOLVE™ in a presence of 0.07 kg (0.72 mol) of sulfuric acid. Heptane (1.7 kg) is added in the process of preparation in order to enhance water entrainment from the reactor. The esterification reaction is carried out at 125 to 150° C. over 13 to 15 hours with continuous removal of water by co-distillation with heptane. Following the reaction, the solution is cooled and the pH is adjusted to neutral using 20% aqueous sodium hydroxide. The normalized composition of the crude product from the batch reactor is given in the Table 1.

TABLE 1

Normalized Composition of the Crude Product from Reactor.

| Component name | Mass Fraction |
|---|---|
| LIGHTS | 0.0018 |
| BENZOIC ACID | 0.0009 |
| BUTYL CELLOSOLVE | 0.0463 |
| 2-BUTOXYETHYL BENZOATE | 0.8443 |
| WATER | 0.0070 |
| HEPTANE | 0.0775 |
| HEAVIES | 0.0221 |

COMPARATIVE EXPERIMENT 1

Laboratory Batch Distillation of 2-Butoxyethyl Benzoate (not an Embodiment of the Invention)

The crude product from the reactor is distilled in batch separation process in a column packed with 18" of wire gauze packing. Heptane is removed in the first overhead cut. Benzoic acid is removed in the overhead cut following the cuts containing mostly heptane. Unreacted Butyl CELLOSOLVE™ is removed as a part of the cut following removal of benzoic acid. Subsequent overhead materials contains more than 99.0% wt of 2-butoxyethyl benzoate. The distillation is completed when the amount of heavy impurities in the overhead material increases to about 0.95% wt. This experiment confirms that 2-butoxyethyl benzoate can be separated from the crude product by a distillation process.

Despite the fact that the resulting 2-butoxyethyl benzoate has a purity of more than 99.0% wt, it has an unpleasant odor. The malodor is attributed to the presence of a trace amount of butanal, which is known to create a malodor in quantities above 1 part per million (ppm).

COMPARATIVE EXPERIMENT 2

Laboratory Conventional Distillation of 2-Butoxyethyl Benzoate (not an Embodiment of the Invention)

The crude product with the composition shown in Table 1 is distilled in a conventional distillation scheme including a stripper and two sequential distillation columns. In the first step crude, product is sent into the stripper in order to remove most of the lights and heptane. The material produced after the stripping of lights and heptane contains 448 ppm of butanal. This material is sent to the first distillation column where traces of heptane, unreacted Butyl CELLOSOLVE™ and part of the benzoic acid are removed as overhead product. The distillation is performed at 24 mmHg. The bottom product of the first column contains mainly 2-butoxyethyl benzoate, heavier components and 12 ppm of butanal. The bottom product of the first column is fed into the second column where 2-butoxyethyl benzoate is taken as the top product. The distillation is performed at 1 mmHg. The temperature of the reboiler reaches 160° C. The bottom product of the second column contains about 40% wt of 2-butoxyethyl benzoate and 60% wt of heavy components. Analysis of the products of the second distillation column indicates that the overhead product contains 327 ppm of butanal and the bottom product contains 154 ppm of butanal. The significant simultaneous increase of butanal in the overhead and bottom products indicates the formation of butanal in the second column.

EXAMPLE 3

Simulation of Distillation of 2-Butoxyethyl Benzoate in a Dividing Wall Column

The data from Comparative Experiments 1 and 2 are used to develop and validate an ASPEN Plus model of 2-butoxyethyl benzoate distillation. The model is used to simulate 2-butoxyethyl benzoate distillation in a dividing wall column. The schematic of the process is shown in FIG. 1.

The crude glycol ester and entrainer stream enters the optional stripper where the most of entrainer is removed overhead. The crude glycol ester stream from the bottom of the stripper is sent to the dividing wall column where the glycol ester is separated as the middle product. The heavy components are separated as the bottom stream from the dividing wall column. The entrainer, unreacted Butyl CELLOSOLVE™ and lighter components are separated as the overhead products in the streams labeled LIGHTS and NONCONDENSABLES. The formation of butanal in the column reboiler is modeled by introducing a steady stream of butanal in the bottom section of the dividing wall column. The mass flow rate of the butanal stream is estimated using data from Comparative Experiment 2. The results of the simulation are presented in Table 2.

TABLE 2

Results of the Simulation for Example 3.

| Streams of FIG. 1 | HEAVIES | BUTANAL (not shown) | CRUDE GLYCOL ESTER & ENTRAINER (OPTIONAL) | CRUDE GLYCOL ESTER | ENTRAINER | LIGHTS | NON-CONDENSABLES | GLYCOL ESTER |
|---|---|---|---|---|---|---|---|---|
| Temperature C. | 63.3 | | 25 | 137.4 | 137.4 | 47.5 | 47.5 | 144.4 |
| Pressure mmHg | 5.1 | | 760 | 400 | 400 | 5 | 5 | 5.05 |
| Mass Flow lb/hr | 1.412 | 0.021 | 44.092 | 40.819 | 3.274 | 0.286 | 2.57 | 36.573 |
| | | | Components Mass Flow, lb/hr | | | | | |
| BENZOIC ACID | 0.0000 | 0.0000 | 0.0400 | 0.0400 | 0.0000 | 0.0290 | 0.0040 | 0.0068 |
| BUTYL CELLOSOLVE | 0.0000 | 0.0000 | 2.0410 | 1.6440 | 0.3970 | 0.1090 | 1.5350 | 5.1E−08 |

TABLE 2-continued

Results of the Simulation for Example 3.

| Streams of FIG. 1 | HEAVIES | BUTANAL (not shown) | CRUDE GLYCOL ESTER & ENTRAINER (OPTIONAL) | CRUDE GLYCOL ESTER | ENTRAINER | LIGHTS | NON-CONDENSABLES | GLYCOL ESTER |
|---|---|---|---|---|---|---|---|---|
| 2-BUTOXYETHYL BENZOATE | 0.4360 | 0.0000 | 37.2290 | 37.1540 | 0.0750 | 0.1470 | 0.0060 | 36.5658 |
| WATER | 0.0000 | 0.0000 | 0.3110 | 0.0610 | 0.2490 | 0.0010 | 0.0610 | 7.1E−15 |
| HEPTANE | 0.0000 | 0.0000 | 3.4170 | 0.9150 | 2.5010 | 0.0010 | 0.9150 | 4.1E−12 |
| HEAVIES | 0.9760 | 0.0000 | 0.9760 | 0.9760 | 0.0000 | 0.0000 | 0.0000 | 7.9E−08 |
| BUTANAL | trace | 0.0210 | 0.0790 | 0.0290 | 0.0510 | 0.0000 | 0.0490 | 1.9E−05 |
| | | | Components Mass Fractions | | | | | |
| BENZOIC ACID | 0.0000 | 0.0000 | 0.0010 | 0.0010 | 0.0000 | 0.1020 | 0.0010 | 187 ppm |
| BUTYL CELLOSOLVE | 0.0000 | 0.0000 | 0.0460 | 0.0400 | 0.1210 | 0.3800 | 0.5970 | trace |
| 2-BUTOXYETHYL BENZOATE | 0.3090 | 0.0000 | 0.8440 | 0.9100 | 0.0230 | 0.5130 | 0.0020 | 0.9998 |
| WATER | 0.0000 | 0.0000 | 0.0070 | 0.0020 | 0.0760 | 0.0020 | 0.0240 | trace |
| HEPTANE | 0.0000 | 0.0000 | 0.0770 | 0.0220 | 0.7640 | 0.0020 | 0.3560 | trace |
| HEAVIES | 0.6910 | 0.0000 | 0.0220 | 0.0240 | 0.0000 | 0.0000 | 0.0000 | 2 ppm |
| BUTANAL | trace | 1.0000 | 0.0020 | 0.0010 | 0.0150 | 0.0000 | 0.0190 | 0.522 ppm |

As shown in Table 2, the distilled 2-butoxyethyl benzoate (stream GLYCOL ESTER) contains only 0.552 ppm of butanal, which is a surprisingly small amount.

COMPARATIVE EXPERIMENT 4

Simulation Of Conventional Distillation Of 2-Butoxyethyl Benzoate (Not An Embodiment Of The Invention)

The model of Example 3 is used to simulate the 2-butoxyethyl benzoate distillation in a conventional separation scheme. The schematic of the process is shown in FIG. 2. As in Example 3, the crude glycol ester and entrainer stream enters the optional stripper in order to remove most of the entrainer and lights from the material. The crude glycol ether stream from the bottom of the stripper is identical to the crude glycol ether stream from Example 3. This stream enters the first distillation column where the lights including entrainer and non-reacted Butyl CELLOSOLVE™ are separated as the overhead product, stream LIGHTS.

The bottom product containing glycol ester and heavies enters the second distillation column where 2-butoxyethyl benzoate is separated as the overhead product, stream GLYCOL ESTER. The bottom product has a composition similar to the bottom product in Example 3. As in Example 3, a steady butanal stream is fed into the reboiler of the second column. The stream is identical to the butanal stream in Example 3. The results of the simulation are presented in Table 3.

The most striking difference between the results of Example 3 and Comparative Experiment 4 is the amount of butanal in the final product streams. The amount of butanal in the product stream of Comparative Experiment 4 is about 100 times higher than the amount of butanal in Example 3. On the other hand, the amount of butanal in the product streams of Comparative Experiments 2 and 4 are on the same order of magnitude, which indicates the model is capable of predicting the actual behavior of the system.

The comparison of operation conditions, equipment configurations and energy consumptions for Example 3 and Comparative Experiment 4 are shown in Table 4. The data indicate that, at similar operating conditions and a similar number of stages, both distillation schemes surprisingly use practically the same amount of energy. This comparison emphasizes an even more surprising advantage, namely that a dividing wall column can be used for production of ultra pure 2-butoxyethyl benzoate or similar glycol esters. The dividing wall configuration provides an additional advantage due to the lower capital cost of equipment compared to the conventional distillation scheme.

TABLE 3

Results of the Simulation for Comparative Experiment 4.

| Streams of FIG. 2 | BUTANAL (stream not shown) | CRUDE GLYCOL ESTER & ENTRAINER (OPTIONAL) | CRUDE GLYCOL ESTER | ENTRAINER | GLYCOL ESTER & HEAVIES | LIGHTS | HEAVIES | GLYCOL ESTER |
|---|---|---|---|---|---|---|---|---|
| Temperature C. | | 25 | 137.4 | 137.4 | 146.6 | 42 | 158.9 | 117.3 |
| Pressure mmHg | | 760 | 400 | 400 | 5.52 | 5 | 5.23 | 5 |
| Mole Flow lbmol/hr | 0 | 0.24 | 0.197 | 0.043 | 0.17 | 0.002 | 0.005 | 0.164 |
| Mass Flow lb/hr | 0.021 | 44.092 | 40.819 | 3.274 | 38.084 | 0.273 | 1.639 | 36.467 |
| | | | Components Mass Flow, lb/hr | | | | | |
| BENZOIC ACID | 0.0000 | 0.0400 | 0.0400 | 0.0000 | 0.0340 | 0.0060 | 0.0000 | 0.0335 |
| BUTYL CELLOSOLVE | 0.0000 | 2.0410 | 1.6440 | 0.3970 | 0.0000 | 0.1880 | 0.0000 | 1.1E−05 |

TABLE 3-continued

Results of the Simulation for Comparative Experiment 4.

| Streams of FIG. 2 | BUTANAL (stream not shown) | CRUDE GLYCOL ESTER & ENTRAINER (OPTIONAL) | CRUDE GLYCOL ESTER | ENTRAINER | GLYCOL ESTER & HEAVIES | LIGHTS | HEAVIES | GLYCOL ESTER |
|---|---|---|---|---|---|---|---|---|
| 2-BUTOXYETHYL BENZOATE | 0.0000 | 37.2290 | 37.1540 | 0.0750 | 37.0740 | 0.0770 | 0.6620 | 36.4120 |
| WATER | 0.0000 | 0.3110 | 0.0610 | 0.2490 | 0.0000 | 0.0010 | 0.0000 | 1.6E-12 |
| HEPTANE | 0.0000 | 3.4170 | 0.9150 | 2.5010 | 0.0000 | 0.0010 | 0.0000 | 9.3E-10 |
| HEAVIES | 0.0000 | 0.9760 | 0.9760 | 0.0000 | 0.9760 | 0.0000 | 0.9760 | 8.9E-07 |
| BUTANAL | 0.0210 | 0.0790 | 0.0290 | 0.0510 | 0.0000 | 0.0000 | 5.9E-07 | 0.020999 |
| | | | | Components Mass Fractions | | | | |
| BENZOIC ACID | 0.0000 | 0.0010 | 0.0010 | 0.0000 | 0.0010 | 0.0210 | 0.0000 | 919 ppm |
| BUTYL CELLOSOLVE | 0.0000 | 0.0460 | 0.0400 | 0.1210 | 0.0000 | 0.6880 | 0.0000 | trace |
| 2-BUTOXYETHYL BENZOATE | 0.0000 | 0.8440 | 0.9100 | 0.0230 | 0.9730 | 0.2830 | 0.4040 | 0.9985 |
| WATER | 0.0000 | 0.0070 | 0.0020 | 0.0760 | 0.0000 | 0.0050 | 0.0000 | trace |
| HEPTANE | 0.0000 | 0.0770 | 0.0220 | 0.7640 | 0.0000 | 0.0030 | 0.0000 | trace |
| HEAVIES | 0.0000 | 0.0220 | 0.0240 | 0.0000 | 0.0260 | 0.0000 | 0.5960 | trace |
| BUTANAL | 1.0000 | 0.0020 | 0.0010 | 0.0150 | 0.0000 | 0.0000 | 0.589 ppm | 576 ppm |

TABLE 4

Comparison of Operation Conditions, Equipment Configurations and Energy Consumptions for Example 3 and Comparative Experiment 4.

| | | Ex. 3 | C.E. 4 Column 1 | C.E. 4 Column 2 |
|---|---|---|---|---|
| Pressure | mmHg | 5 | 5 | 5 |
| Number of stages | | 12 | 6 | 10 |
| Reflux ratio | mole/mole | 6.22 | 0.76 | 0.06 |
| Condenser heat load | Btu/hr | −6346 | −798 | −5862 |
| Reboiler heat load | Btu/hr | 6776 | 1249 | 5039 |
| Product rate | lb/hr | 36.6 | | 36.5 |
| Cooling energy per unit product weight | Btu/lb | −174 | | −183 |
| Heating energy per unit product weight | Btu/lb | 185 | | 172 |

EXAMPLE 5

Simulation of Distillation of 2-Butoxyethyl Benzoate in a Separation Train with Pasteurization The model of Example 3 is used to simulate 2-butoxyethyl benzoate distillation in a separation train with a pasteurization column. The schematic of the process is shown in FIG. 3. As in Example 3 and Comparative Experiment 4, the crude glycol ester and entrainer stream enters the optional stripper in order to remove most of the entrainer and lights from the material. The crude glycol ester stream from the bottom of the stripper is identical to the crude glycol ester stream from Example 3 and Comparative Experiment 4. This stream enters the first distillation column where the lights, including entrainer and unreacted Butyl CELLOSOLVE™, are separated as the overhead product, stream LIGHTS.

The bottom product containing glycol ether and heavies enters the second distillation column, which is equipped with a pasteurization section at the top. In this column 2-butoxyethyl benzoate is separated as an intermediate (middle) product right below the pasteurization section, stream GLYCOL ESTER. The top products of the second column are noncondensed lights, stream NONCONDENSABLES, and lighter condensable components including butanal, stream LIGHTS 2. The composition of the bottom product is similar to that of the bottom product of Example 3. As in Example 3 and Comparative Experiment 4, a steady butanal stream is fed to the reboiler of the second column. The stream is identical to the butanal stream in the Example 3 and Comparative Experiment 4. The results of the simulation are presented in Table 5.

TABLE 5

Results of the Simulation for Example 5.

| Stream name | BUTANAL (stream not shown) | CRUDE GLYCOL ESTER & ENTRAINER (OPTIONAL) | CRUDE GLYCOL ESTER | EN-TRAINER | GLYCOL ESTER & HEAVIES | LIGHTS | LIGHTS 2 | NON-CONDENS-ABLES | HEAVIES | GLYCOL ETHER |
|---|---|---|---|---|---|---|---|---|---|---|
| Temperature C. | | 25 | 137.4 | 137.4 | 146.6 | 42 | 130.4 | 130.4 | 186 | 144.4 |
| Pressure mmHg | | 760 | 400 | 400 | 5.52 | 5 | 5 | 5 | 5.3 | 5.06 |
| Mole Flow lbmol/hr | 0 | 0.24 | 0.197 | 0.043 | 0.17 | 0.027 | 0.008 | 0.001 | 0.003 | 0.158 |
| Mass Flow lb/hr | 0.021 | 44.092 | 40.819 | 3.274 | 38.084 | 2.735 | 1.809 | 0.095 | 1.098 | 35.103 |
| | | | | | Components Mass Flow lb/hr | | | | | |
| BENZOIC ACID | 0.0000 | 0.0400 | 0.0400 | 0.0000 | 0.0340 | 0.0060 | 0.0170 | 0.0040 | 0.0000 | 0.012 |
| BUTYL CELLOSOLVE | 0.0000 | 2.0410 | 1.6440 | 0.3970 | 0.0000 | 1.6440 | 0.0000 | 0.0000 | 0.0000 | trace |

TABLE 5-continued

Results of the Simulation for Example 5.

| Stream name | BUTANAL (stream not shown) | CRUDE GLYCOL ESTER & ENTRAINER (OPTIONAL) | CRUDE GLYCOL ESTER | EN-TRAINER | GLYCOL ESTER & HEAVIES | LIGHTS | LIGHTS 2 | NON-CONDENS-ABLES | HEAVIES | GLYCOL ETHER |
|---|---|---|---|---|---|---|---|---|---|---|
| BUTOXYETHYL BENZOATE | 0.0000 | 37.2290 | 37.1540 | 0.0750 | 37.0740 | 0.0800 | 1.7910 | 0.0710 | 0.1220 | 35.09 |
| WATER | 0.0000 | 0.3110 | 0.0610 | 0.2490 | 0.0000 | 0.0610 | 0.0000 | 0.0000 | 0.0000 | trace |
| HEPTANE | 0.0000 | 3.4170 | 0.9150 | 2.5010 | 0.0000 | 0.9150 | 0.0000 | 0.0000 | 0.0000 | trace |
| HEAVIES | 0.0000 | 0.9760 | 0.9760 | 0.0000 | 0.9760 | 0.0000 | 0.0000 | 0.0000 | 0.9760 | 7.60E−11 |
| BUTANAL | 0.0210 | 0.0790 | 0.0290 | 0.0510 | 0.0000 | 0.0290 | 0.0000 | 0.0210 | 0.0000 | 3.10E−07 |
| Components Mass Fractions | | | | | | | | | | |
| BENZOIC ACID | 0.0000 | 0.0010 | 0.0010 | 0.0000 | 0.0010 | 0.0020 | 0.0090 | 0.0420 | 0.0000 | 353 ppm |
| BUTYL CELLOSOLVE | 0.0000 | 0.0460 | 0.0400 | 0.1210 | 0.0000 | 0.6010 | 0.0000 | 0.0000 | 0.0000 | trace |
| BUTOXYETHYL BENZOATE | 0.0000 | 0.8440 | 0.9100 | 0.0230 | 0.9730 | 0.0290 | 0.9900 | 0.7430 | 0.1110 | 0.9996 |
| WATER | 0.0000 | 0.0070 | 0.0020 | 0.0760 | 0.0000 | 0.0220 | 0.0000 | 0.0000 | 0.0000 | trace |
| HEPTANE | 0.0000 | 0.0770 | 0.0220 | 0.7640 | 0.0000 | 0.3350 | 0.0000 | 0.0000 | 0.0000 | trace |
| HEAVIES | 0.0000 | 0.0220 | 0.0240 | 0.0000 | 0.0260 | 0.0000 | 0.0000 | 0.0000 | 0.8890 | trace |
| BUTANAL | 1.0000 | 0.0020 | 0.0010 | 0.0150 | 0.0000 | 0.0100 | 0.0000 | 0.2150 | 0.0000 | 0.647 ppm |

As in Example 3, the amount of butanal in the final product is very small at 0.647 ppm. These results indicate that the separation scheme using a pasteurization column is capable of achieving results similar to those of the dividing wall column.

The comparison of energy consumption, equipment configurations and operation conditions between Examples 3 and 5 is shown in Table 6.

TABLE 6

Comparison of Operation Conditions, Equipment Configurations and Energy Consumptions for Examples 3 and 5.

| | | Ex. 3 | Ex. 5 Column 1 | Ex. 5 Column 2 |
|---|---|---|---|---|
| Pressure | mmHg | 5 | 5 | 5 |
| Number of stages | | 12 | 6 | 12 |
| Reflux ratio | mole/mole | 6.22 | 0.75 | 18.87 |
| Condenser heat load | Btu/hr | −6346 | −798 | −5483 |
| Reboiler heat load | Btu/hr | 6776 | 1249 | 5449 |
| Product rate | lb/hr | 36.6 | 38.08 | 35.1 |
| Cooling energy per unit product weight | Btu/lb | −174 | | −179 |
| Heating energy per unit product weight | Btu/lb | 185 | | 191 |

The data in the table indicate very similar energy consumption between the two configurations. One advantage of the dividing wall column is the lower capital cost of the equipment. On the other hand, a pasteurizing section can be implemented in an existing conventional distillation train.

What is claimed is:

1. A process for the production of 2-butoxyethyl benzoate, the process comprising: (a) contacting benzoic acid and 2-butoxy ethanol under reaction conditions to produce a crude product comprising 2-butoxyethyl benzoate and impurities; (b) feeding at least a portion of the crude product to a distillation column comprising a dividing wall or a pasteurizing section; removing an overhead stream and a bottoms stream from the distillation column, and removing a side draw stream from the distillation column; wherein, in the case where a dividing wall is present, the crude product enters the dividing wall distillation column on an opposing side of the dividing wall from the side draw stream.

2. The process of claim 1 wherein one of the impurities is butanal.

3. The process of claim 1 wherein the side draw stream comprises 2-butoxyethyl benzoate and less than 5 part per million of butanal.

4. The process of claim 1 wherein the side draw stream comprises more than 99.0% wt 2-butoxyethyl benzoate.

5. The process of claim 1 wherein the contacting of step (a) is conducted in the presence of an acid catalyst.

6. The process of claim 1 wherein the distillation column comprises a dividing wall.

7. The process of claim 1 wherein the distillation column comprises a pasteurizing section.

8. The process of claim 1 wherein an entrainer is present in the crude product.

9. The process of claim 1 wherein the entrainer is substantially removed from the crude product in an optional stripper.

10. The process of claim 1 wherein the side draw stream comprises 2-butoxyethyl benzoate and less than 1 part per million of butanal.

* * * * *